(12) United States Patent
Kagechika et al.

(10) Patent No.: US 6,458,782 B1
(45) Date of Patent: Oct. 1, 2002

(54) REMEDIES FOR DIABETES

(75) Inventors: Hiroyuki Kagechika; Yuichi Hashimoto; Hideji Fujii; Yoshiaki Yonekawa; Hisao Ekimoto, all of Tokyo (JP)

(73) Assignee: Institute of Medicinal Molecular Design, Inc., Tokyo (JP)

(*) Notice: Subject to any disclaimer, the term of this patent is extended or adjusted under 35 U.S.C. 154(b) by 0 days.

(21) Appl. No.: 09/555,508

(22) PCT Filed: Dec. 4, 1998

(86) PCT No.: PCT/JP98/05480

§ 371 (c)(1),
(2), (4) Date: Sep. 1, 2000

§ 102(e) Date: Sep. 1, 2000

(87) PCT Pub. No.: WO99/29324

PCT Pub. Date: Jun. 17, 1999

(30) Foreign Application Priority Data

Dec. 5, 1997 (JP) .............................. 9/335956

(51) Int. Cl.[7] .................. A61K 31/55; A61K 38/28; A61K 31/425
(52) U.S. Cl. .................. 514/217; 514/220; 514/3; 514/369; 514/866
(58) Field of Search .................. 514/217, 220, 514/3, 369, 866

(56) References Cited

U.S. PATENT DOCUMENTS

| 5,929,069 A | 7/1999 | Shudo ......................... 514/219 |
| 6,121,256 A | 9/2000 | Shudo .................... 514/211.04 |

FOREIGN PATENT DOCUMENTS

| JP | 9100270 | 4/1997 |
| JP | 10114757 | * 5/1998 |
| WO | 97/12853 | 4/1997 |
| WO | 98/45242 | 10/1998 |

OTHER PUBLICATIONS

An English Language abstract of JP 9–100270.
An English Language abstract of JP 10–114757.
Budavari et al., The Merck Index, Twelfth Edition (1996) pp. 855, 856 and 1282, abstract nos. 5011 and 7605.*

* cited by examiner

Primary Examiner—Kevin E. Weddington
(74) Attorney, Agent, or Firm—Greenblum & Bernstein, P.L.C.

(57) ABSTRACT

Medicaments comprising a compound represented by the following formulas:

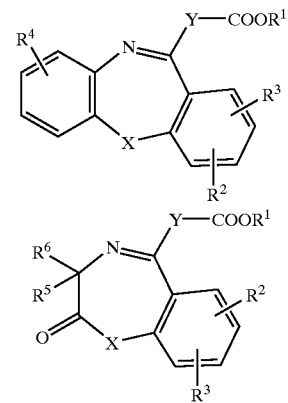

wherein, $R^1$ represents hydrogen atom or a $C_{1-6}$ alkyl group; $R^2$ and $R^3$ represent hydrogen atom or a $C_{1-6}$ alkyl group, or $R^2$ and $R^3$ may combine together with the carbon atoms of the phenyl ring to which $R^2$ and $R^3$ bind to represent a 5- or 6-membered ring; $R^4$ represents hydrogen atom, a $C_{1-6}$ alkyl group, a $C_{1-6}$ alkoxyl group etc.; $R^5$ represents hydrogen atom, a $C_{1-6}$ alkyl group, or an aryl-substituted $C_{1-6}$ alkyl group; $R^6$ represents hydrogen atom or a $C_{1-6}$ alkyl group; X represents —$NR^7$—, —NO—, —O— etc. in which $R^7$ represents hydrogen atom, a $C_{1-6}$ alkyl group etc.; and Y represents a phenylene group or a pyridinediyl group, which are useful for preventive and therapeutic treatments of diabetes and complications of diabetes.

20 Claims, No Drawings

REMEDIES FOR DIABETES

BACKGROUND OF THE INVENTION

1. Field of the Invention

The present invention relates to a medicament useful for preventive and/or therapeutic treatment of diabetes and complications thereof and to a method for preventive and/or therapeutic treatment of diabetes and complications thereof.

2. Discussion of Background Information

As medicaments for treatment of diabetes that can be orally administered, sulfonylurea-type drugs or biguanide-type drugs have conventionally been used. However, sulfonylurea-type drugs are known to cause critical and prolonged hypoglycemia, and biguanide-type drugs cause critical lactic acidosis or hypoglycemia. Therefore, administration of these drugs requires sufficient precautions with respect to doses, methods of administration and so forth.

It has been reported that thiazoline derivatives have hypoglycemic activity (Japanese Patent Unexamined Publication [Kokai] Nos. 61-85372/1986, 60-51189/1985 and the like), and they have been clinically used as medicament for treatment of diabetes having overcome the aforementioned drawbacks. However, because of the diversity of origins of diabetes, thiazoline derivatives cannot always exhibit sufficient curative effects for all patients with diabetes (Diabetes Care, 19, 151). Therefore, it has been desired to develop medicament for treatment of diabetes with still higher effectiveness.

Benzodiazepine derivatives such as 4-[5H-2,3-(2,5-dimethyl-2,5-hexano)-5-methyldibenzo[b,e][1,4]diazepin-11-yl]benzoic acid and 4-[1,3-dihydro-7,8-(2,5-dimethyl-2,5-hexano)-2-oxo-2H-1,4-benzodiazepin-5-yl]benzoic acid have been known (PCT/JP96/2709, International Publication WO97/11061). These compounds have activity for markedly enhancing the action of retinoids such as retinoic acid, while the compounds, per se, have no retinoid action or their retinoid actions are very weak, and they are suggested to be useful for therapeutic and preventive treatment of vitamin A deficiency disease, hyperkeratosis of epithelial tissue, rheumatism, delayed allergy, bone disease, leukemia and certain types of cancer. However, the aforementioned publications neither teach nor suggest that the aforementioned compounds are useful for therapeutic or preventive treatment of diabetes.

SUMMARY OF THE INVENTION

The present invention provides a medicament useful for therapeutic and/or preventive treatment of diabetes. The present invention also provides a medicament useful for therapeutic and/or preventive treatment of complications of diabetes such as hyperlipidemia. The present invention further provides a medicament having such characteristics as mentioned above, which can achieve the therapeutic and/or preventive effects by oral administration, and have reduced or no side effects such as hypoglycemic shock.

Various studies were conducted, and as a result, it was discovered that the benzodiazepine derivatives disclosed in International Publication WO 97/11061 (PCT/JP96/2709) had an excellent action for enhancing differentiation of precursor adipocytes and excellent hypoglycemic action. It was also discovered that those compounds were useful for therapeutic and/or preventive treatment of diabetes, and that when they were used in combination with thiazoline compounds or insulin-like compounds, agents conventionally used for treatment of diabetes, the aforementioned therapeutic and preventive effects were synergistically enhanced.

The present invention thus provides agents for therapeutic and/or preventive treatment of diabetes, which comprise, as an active ingredient, a substance selected from compounds represented by the following general formula (I):

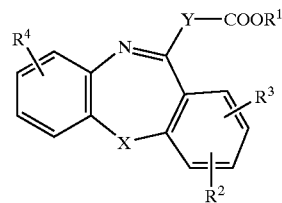

or compounds represented by the following general formula (II):

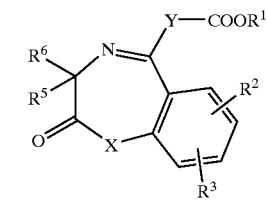

wherein, $R^1$ represents hydrogen atom or a $C_{1-6}$ alkyl group; $R^2$, and $R^3$ independently represent hydrogen atom or a $C_{1-6}$ alkyl group, or $R^2$ and $R^3$ may combine together with carbon atoms of the phenyl ring to which $R^2$ and $R^3$ bind to represent a 5- or 6-membered ring which may optionally be substituted with one or more $C_{1-4}$ alkyl groups; $R^4$ represents hydrogen atom, a $C_{1-6}$ alkyl group, a $C_{1-6}$ alkoxyl group, hydroxyl group, nitro group, or a halogen atom; $R^5$ represents hydrogen atom, a $C_{1-6}$ alkyl group, or an aryl-substituted $C_{1-6}$ alkyl group; $R^6$ represents hydrogen atom or a $C_{1-6}$ alkyl group; X represents —$NR^7$—, —NO—, —O—, —$CHR^7$—, —S—, —SO— or —$SO_2$— in which $R^7$ represents hydrogen atom, a $C_{1-6}$ alkyl group, or an aryl-substituted $C_{1-6}$ alkyl group; and Y represents a phenylene group or a pyridinediyl group, physiologically acceptable salts thereof, and hydrates thereof and solvates thereof According to another aspect of the present invention, there are provided medicaments for therapeutic and/or preventive treatment of complications of diabetes (for example, hyperlipidemia), which comprise the aforementioned substance as an active ingredient. There are further provided the aforementioned therapeutic and/or preventive medicament, which are used in combination with an agent for therapeutic and/or preventive treatment of diabetes selected from the group consisting of thiazoline compounds and substances having insulin-like action; medicaments for therapeutic and/or preventive treatment of diabetes, which are in the form of a pharmaceutical composition comprising the aforementioned substance and an agent for therapeutic and/or preventive treatment of diabetes which is selected from the group consisting of thiazoline compounds and substances having insulin-like action; medicaments for therapeutic and/or preventive treatment of complications of diabetes, which are in the form of a pharmaceutical composition comprising the aforementioned substance and an agent for therapeutic and/or preventive treatment of diabetes selected from the group consisting of thiazoline compounds and substances having insulin-like action; and the aforementioned therapeutic and/or preventive medicaments, which are used as an agent to enhance the action of an agent for therapeutic and/or preventive treatment of diabetes selected from the group consisting of thiazoline compounds and substances having insulin like action.

According to further aspects of the present invention, there are provided use of the aforementioned substance for the manufacture of the aforementioned therapeutic and/or preventive medicaments; and methods for therapeutic and/or preventive treatment of diabetes or complications thereof, which comprises the step of administering an effective amount of the aforementioned substance to a mammal including human.

DETAILED DESCRIPTION OF THE PRESENT INVENTION

The present invention concerns a medicament which comprises a compound represented by the aforementioned formula (I) or (II) as an active ingredient, and is used for therapeutic and/or preventive treatment of diabetes or therapeutic and/or preventive treatment of complications of diabetes.

In the above general formulae, $R^1$ represents hydrogen atom or a linear or branched $C_{1-6}$ (i.e., having 1 to 6 carbon atoms) alkyl group. Examples of the alkyl group include, for example, methyl group, ethyl group, n-propyl group, isopropyl group, n-butyl group, sec-butyl group, and tert-butyl group, and methyl group is preferably used. $R^2$ and $R^3$ independently represent hydrogen atom or a linear or branched $C_{1-6}$ alkyl group. As for the alkyl group, those mentioned above may be used, and ethyl group, isopropyl group, tert-butyl group or the like may preferably be used. The substituting positions of $R^2$ and $R^3$ are not particularly limited, and each of them may independently substitute at any position. It is preferred that $R^2$ and $R^3$ are in para-position and meta-position with reference to X, respectively, or $R^2$ and $R^3$ are in meta-position and ortho-position with reference to X. It is particularly preferred that $R^2$ and $R^3$ are in para-position and meta-position with reference to X, respectively.

$R^2$ and $R^3$ may combine to form a 5- or 6-membered ring together with two carbon atoms on the phenyl ring to which each of $R^2$ and $R^3$ binds. The cycloakyl ring may have one or more $C_{1-4}$ alkyl groups. For example, the ring may have from two to four methyl groups, preferably four methyl groups. It is preferred that, for example, $R^2$ and $R^3$ together with the phenyl ring substituted with $R^2$ and $R^3$ form 5,6,7,8-tetrahydronaphthalene ring or 5,5,8,8-tetramethyl-5,6,7,8-tetrahydronapthalene ring.

$R^4$ represents hydrogen atom, a $C_{1-6}$ alkyl group, a $C_{1-6}$ alkoxyl group, hydroxyl group, nitro group, or a halogen atom. As the $C_{1-6}$ alkyl group, these exemplified above may be used. As the $C_{1-6}$ alkoxyl group, for example, methoxy group, ethoxy group, n-propoxy group, isopropoxy group, n-butoxy group, sec-butoxy group, or tert-butoxy group, preferably methoxy group, may be used. As the halogen atom, any of fluorine atom, chlorine atom, bromine atom, or iodine atom may be used. The position of $R^4$ is not particularly limited, and it may substitute at any position on the phenyl ring.

$R^5$ represents hydrogen atom, a $C_{1-6}$ alkyl group, or an aryl-substituted $C_{1-6}$ alkyl group. The $C_{1-6}$ alkyl group may be either linear or branched, and those mentioned above may preferably be used. Examples of the aryl moiety of the aryl-substituted $C_{1-6}$ alkyl group include, for example, phenyl, naphthyl, or pyridyl group, and the $C_{1-6}$ alkyl moiety may be either linear or branched. For example, a phenyl-substituted $C_{1-6}$ alkyl group such as benzyl group or phenethyl group, a naphthyl-substituted $C_{1-6}$ alkyl group such as naphthylmethyl group, a pyridyl-substituted $C_{1-6}$ alkyl group such as pyridylmethyl group and the like can be used.

The aryl group constituting these aryl-substituted $C_{1-6}$ alkyl groups may have one or more substituents. For example, a halogen atom such as fluorine atom or chlorine atom; a $C_{1-6}$ alkyl group such as methyl group or ethyl group; a linear or branched $C_{1-6}$ alkoxyl group such as methoxy group or ethoxy group; nitro group; a linear or branched halogenated $C_{1-6}$ alkyl group such as trifluoromethyl group; hydroxyl group; carboxyl group; a $C_{1-6}$ alkoxycarbonyl group such as methoxycarbonyl group or ethoxycarbonyl group or the like may be used as the substituent. $R^6$ represents hydrogen atom or a $C_{1-6}$ alkyl group. The $C_{1-6}$ alkyl group may be either linear or branched, and those explained above may preferably be used. The compounds wherein both of $R^5$ and $R^6$ are hydrogen atoms, and the compounds wherein $R^6$ is a $C_{1-6}$ alkyl group or an aryl-substituted $C_{1-6}$ alkyl group and $R^6$ is hydrogen atom are particularly preferred compounds.

X represents a nitrogen atom substituted with $R^7$ (—$NR^7$—), an oxygen atom (—O—), a methylene group substituted with $R^7$ (—$CHR^7$—), or a sulfur atom (—S—). $R^7$ represents hydrogen atom, a $C_{1-6}$ alkyl group, or an aryl-substituted $C_{1-6}$ alkyl group. The $C_{1-6}$ alkyl group may be either linear or branched, and those exemplified above, e.g., methyl group, may be used. As the aryl-substituted $C_{1-6}$ alkyl group, those exemplified above, preferably benzyl group, may be used. The nitrogen atom and the sulfur atom may be in the form of an oxide (—NO—, —SO— or —$SO_2$—). Among them, X is preferably a nitrogen atom substituted with $R^7$ ($NR^7$), and X most preferably represents a nitrogen atom substituted with methyl group, ethyl group, n-propyl group, isopropyl group, or benzyl group.

Y represents a phenylene group or a pyridinediyl group. For example, any one of phenylene groups or pyridinediyl groups such as p-phenylene group, m-phenylene group, o-phenylene group, pyridine-2,4-diyl group, pyridine-2,5-diyl group, or pyridine-3,5-diyl group may be used. Preferably, p-phenylene group, m-phenylene group, or pyridine-2,5-diyl group may be used. Where pyridine-2,5-diyl group is used, the group represented by —$COOR^1$ may substitute either at 2-position or 5-position of the pyridine ring.

As the active ingredient of the medicament of the present invention, the aforementioned compounds in the free forms, or physiologically acceptable acid addition salts and base addition salts thereof may be used. Examples of the physiologically acceptable acid addition salts include mineral acid salts such as hydrochloride or hydrobromide, and organic acid salts such as p-toluenesulfonate, methanesulfonate, oxalate, or tartrate. The base addition salts may be formed when $R^1$ represents hydrogen atom. Metal salts such as, for example, sodium salt, potassium salt, magnesium salt, or calcium salt, ammonium salts, or organic amine salts such as, for example, triethylamine salt or ethanolamine salt may be used.

As for the compounds of the present invention represented by the formula (II), where $R^5$ and $R^6$ are different substituents to each other, the carbon atom substituted thereby is recognized. as an asymmetric carbon atom. On the assumption that the 7-membered ring containing X forms a plane, in the formula (II), either $R^5$ or $R^6$ may be above the plane. In addition, the compounds of the formula (I) and the formula (II) of the present invention may have one or more additional asymmetric carbon atoms depending on types of X and other substituents. Any optical isomers based on the asymmetric carbon atom(s), any mixture of optical isomers, racemates, any diastereomers based on two or more asymmetric carbons, any mixtures of the diastereomers and the like may be used as the active ingredient of the medicament of the present invention. It should also be understood that any hydrates or solvates of the compounds in the free forms or those of the compounds in the forms of salts may also be used as the active ingredient of the medicament of the present invention.

Among the compounds represented by the above formula (I), examples of the compounds preferred as the active ingredient of the medicament of the present invention include:

4-[5H-2,3-(2,5-dimethyl-2,5-hexano)-5-methyldibenzo [b,e][1,4]diazepin-11-yl]benzoic acid (HX600);

4-[5H-2,3-diisopropyl-5-methyldibenzo[b,e][1,4] diazepin- 11-yl]benzoic acid (HX610);

4-[5H-2-tert-butyl-5-methyldibenzo[b,e][1,4]diazepin- 11-yl]benzoic acid (HX511);

4-[5H-3,4-(1,4-butano)-5-methyldibenzo[b,e][1,4] diazepin-11-yl]benzoic acid (HX545);

4-[5H-2,3-(2,5-dimethyl-2,5-hexano)-5-methyl-8-nitrodibenzo[b,e][1,4]-diazepin-11-yl]benzoic acid (HX531);

4-[2,3-(2,5-dimethyl-2,5-hexano)dibenzo[b,f][1,4] oxazepin-11-yl]benzoic acid (HX620);

4-[2,3-(2,5-dimethyl-2,5-hexano)dibenzo[b,f][1,4] thiazepin-11-yl]benzoic acid (HX630);

5-[5H-2,3-(2,5-dimethyl-2,5-hexano)-5-methyldibezzo [b,e][1,4]diazepin-11-yl]-2-pyridinecarboxylic acid;

6-[5H-2,3-(2,5-dimethyl-2,5-hexano)-5-methyldibenzo [b,e][1,4]diazepin-11-yl]-3-pyridinecarboxylic acid; and 4-[2,3-(2,5-dimethyl-2,5-hexano)dibenzo[b,e]azepin-11-yl]benzoic acid (HX640), and lower alkyl esters of the above respective compounds, preferably methyl esters (for example, as to HX600, methyl 4-[5H-2,3(2,5-dimethyl-2,5-hexano)-5-methyldibenzo-[b,e][1,4]diazepin-11-yl]benzoate).

Among the compounds represented by the formula (II), examples of the compounds preferred as the active ingredient of the medicament of the present invention include, for example, those listed in the table set out below. In these compounds, $R^1$ is hydrogen atom or methyl group, Y is p-phenylene group, and X is —$NR^7$—. The abbreviation "Bzl" represents benzyl group, and descriptions such as 7-Me, 8-Et, 8-i-Pro, and 9-t-Bu represent that the compounds of formula (II) is substituted with methyl group at the 7-position, ethyl group at the 8-position, isopropyl group at the 8-position, and tert-butyl group at the 9-position, respectively. The descriptions such as 7—$(CH_2)_4$-8 and 7—$C(CH_3)_2CH_2CH_2C(CH_3)_2$-8 represent that the 7-position and the 8-position of the compounds of the formula (II) are bound with —$(CH_2)_4$— and —$C(CH_3)_2CH_2CH_2C(CH_3)_2$—, respectively.

TABLE 1

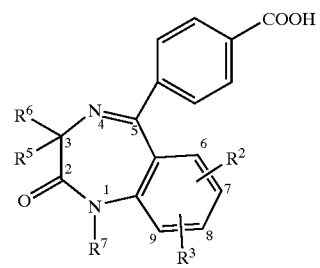

| $R^2$ | $R^3$ | $R^5$ | $R^6$ | $R^7$ |
|---|---|---|---|---|
| H | H | H | H | H |
| 7-Me | H | H | H | H |
| 7-Me | 8-Me | H | H | H |
| 8-Me | 9-Me | H | H | H |
| 7-Et | 8-Et | H | H | H |
| 7-n-Pro | 8-n-Pro | H | H | H |
| 7-i-Pro | 8-i-Pro | H | H | H |
| 7-i-Pro | 8-i-Pro | Me | H | H |
| 7-i-Pro | 8-i-Pro | Et | H | H |
| 7-i-Pro | 8-i-Pro | i-Pro | H | H |
| 7-i-Pro | 8-i-Pro | H | H | Me |
| 7-i-Pro | 8-i-Pro | Me | H | Me |
| 7-i-Pro | 8-i-Pro | Et | H | Me |
| 7-i-Pro | 8-i-Pro | Et | Me | Me |
| 7-i-Pro | 8-i-Pro | i-Pro | H | Me |
| 7-i-Pro | 8-i-Pro | i-Pro | H | i-Pro |
| 7-i-Pro | 8-n-Pro | H | H | H |
| 7-t-Bu | 8-t-Bu | Me | H | H |
| 7-t-Bu | 8-t-Bu | Et | H | H |
| 7-t-Bu | 8-t-Bu | i-Pro | H | H |
| 7-t-Bu | 8-t-Bu | H | H | Me |
| 7-t-Bu | 8-t-Bu | H | H | i-Pro |
| 7-t-Bu | 8-t-Bu | Me | H | Me |
| 7-t-Bu | 8-t-Bu | i-Pro | H | Me |
| 7-t-Bu | 8-t-Bu | Et | Me | Me |
| 7-$C(CH_2)_4$-8 | | H | H | H |
| 7-$C(CH_3)_2CH_2CH_2C(CH_3)_2$-8 | | H | H | H |
| 7-$C(CH_3)_2CH_2CH_2C(CH_3)_2$-8 | | Me | H | H |
| 7-$C(CH_3)_2CH_2CH_2C(CH_3)_2$-8 | | Me | Me | H |
| 7-$C(CH_3)_2CH_2CH_2C(CH_3)_2$-8 | | Me | Me | Me |
| 7-$C(CH_3)_2CH_2CH_2C(CH_3)_2$-8 | | Et | H | H |
| 7-$C(CH_3)_2CH_2CH_2C(CH_3)_2$-8 | | n-Pro | H | H |
| 7-$C(CH_3)_2CH_2CH_2C(CH_3)_2$-8 | | i-Pro | H | H |
| 7-$C(CH_3)_2CH_2CH_2C(CH_3)_2$-8 | | H | H | Me |
| 7-$C(CH_3)_2CH_2CH_2C(CH_3)_2$-8 | | H | H | i-Pro |
| 7-$C(CH_3)_2CH_2CH_2C(CH_3)_2$-8 | | n-Pro | H | Me |
| 7-$C(CH_3)_2CH_2CH_2C(CH_3)_2$-8 | | i-Pro | H | Me |
| 7-$C(CH_3)_2CH_2CH_2C(CH_3)_2$-8 | | i-Pro | H | i-Pro |
| 7-$C(CH_3)_2CH_2CH_2C(CH_3)_2$-8 | | t-Bu | H | H |
| 7-$C(CH_3)_2CH_2CH_2C(CH_3)_2$-8 | | t-Bu | H | Me |
| 7-$C(CH_3)_2CH_2CH_2C(CH_3)_2$-8 | | t-Bu | H | i-Pro |
| 7-$C(CH_3)_2CH_2CH_2C(CH_3)_2$-8 | | Bzl | H | H |
| 7-$C(CH_3)_2CH_2CH_2C(CH_3)_2$-8 | | Bzl | H | Me |
| 7-$C(CH_3)_2CH_2CH_2C(CH_3)_2$-8 | | H | H | Bzl |

Among them, examples of particularly preferred compounds include:

4-[1,3-dihydro-7,8-(2,5-dimethyl-2,5-hexano)-2-oxo-2H-1,4-benzodiazepin-5-yl]benzoic acid (HX800);

4-[1,3-dihydro-7,8-(2,5-dimethyl-2.5-hexano)-1-methyl-2-oxo-2H-1,4-benzodiazepin-5-yl]benzoic acid (HX801);

4-[3(S)-methyl-1,3-dihydro-7,8-(2.5-dimethyl-2,5-hexano)-2-oxo-2H-1,4-benzodiazepin-5-yl]benzoic acid (HX810);

4-[1,3-dihydro-7,8-(2,5-dimethyl-2,5-hexano)-1-isopropyl-2-oxo-2H-1,4-benzodiazepin-5-yl]benzoic acid (HX803);

4-[1-benzyl-1,3-dihydro-7,8-(2,5-dimethyl-2,5-hexano)-2-oxo-2H-1,4-benzodiazepin-5-yl]benzoic acid (HX805); and 4-[3(S)-benzyl-1,3-dihydro-7,8-(2,5-dimethyl-2,5-hexano)-2-oxo-2H-1,4-benzodiazepin-5-yl]benzoic acid (HX850), and lower alkyl ester of each of the above compounds, preferably, methyl esters (for example, as to HX800, methyl 4-[1,3-dihydro-7,8-(2,5-dimethyl-2,5-hexano)-2-oxo-2H-1,4-benzodiazepin-5-yl]benzoate).

HX800
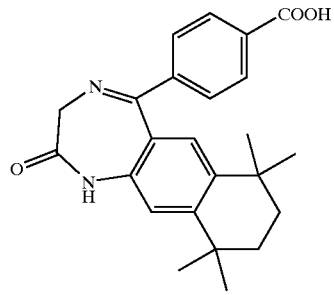

HX801
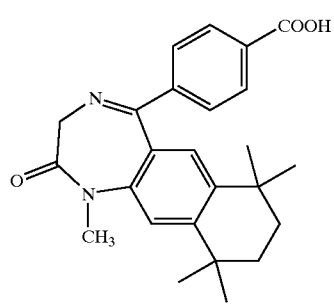

HX810
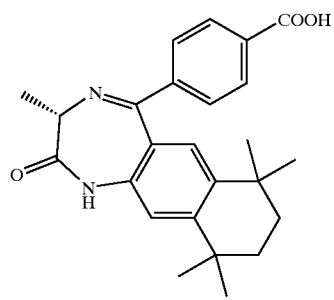

HX803
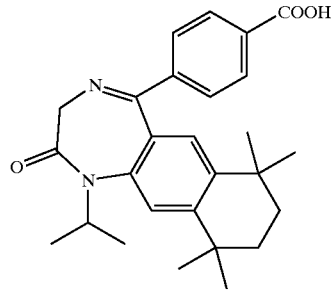

HX805
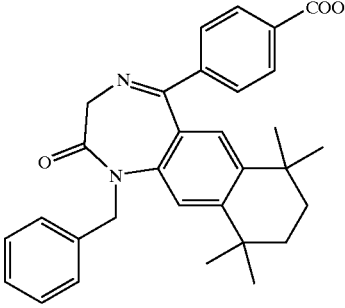

HX850
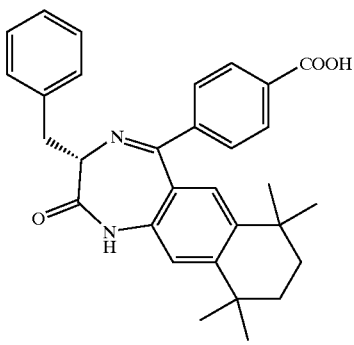

The compounds represented by the aforementioned formulas (I) and (II) are known, and they can easily be prepared, for example, according to the methods disclosed in publications such as International Publication WO 97/11061 (PCT/JP96/2709).

A cause and pathological condition of diabetes treatable by the medicament of the present invention are not particularly limiter For example, both of insulin dependent diabetes mellitus (IDDM) and noninsulin dependent diabetes mellitus (NIDDM) are treatable by the medicament, and in addition, the medicament of the present invention can be applied to diabetes caused by abnormality of insulin action (for example, disorder of intracellular glucose utilization, functional disorder of an insulin receptor, structural abnormality of insulin, and those related to administration of drugs such as glucocorticoid or the like); diabetes caused by abnormality of insulin secretion (abnormality of signal transmission such as mutation of glucokinase gene, partial destruction of pancreatic β-cells due to pancreatitis, autoimmune mechanism or the like); diabetes caused by nutritional disturbance and so forth.

In general, treatment of diabetes is performed to prevent the onset of acute and chronic complications and suppress development thereof. The medicament of the present invention can also be used for preventive and/or therapeutic treatment of complications of diabetes. The term "preventive treatment" used herein should be construed in its broadest sense including prevention of the onset of diabetes or complications thereof. Furthermore, the term "therapeutic treatment" used in the present specification should be construed in its broadest sense including radical therapeutic treatment of diabetes and complications thereof, remission of symptoms, suppression of development of pathological conditions and the like. Examples of the complications of diabetes which are treatable by the medicament of the present invention include, for example, retinopathy, nephropathy, diphtheritic neuropathy, and hyperlipidemia. Among them, hyperlipidemia resulting from diabetes is preferably treatable by the medicament of the present invention.

The medicament of the present invention may be used in combination with one or more other medicaments used for therapeutic and/or preventive treatment of diabetes or therapeutic and/or preventive treatment of complications of diabetes For example, when the medicament of the present invention is used in combination with a thiazoline compound or a substance having insulin-like action used as an agent for treatment of diabetes, the action of the medicament is synergistically enhanced. Therefore, a combined used with these medicaments is a preferred embodiment of the present invention. Examples of the thiazoline compound used as an agent for treatment of diabetes include, for example, troglitazone (Noscal, Sankyo Co., Ltd.), pioglitazone (Japanese Patent Unexamined Publication [Kokai] No. 61-267580/1986), BRL-49653 (Japanese Patent Unexamined Publication [Kokai] No. 1-131169/1989) and the like. Examples of the substance having insulin-like action include, for example, insulin, insulin secretion promoting agents (glimepiride, Hoechst Marion Roussel and other companies). In addition, the medicament may be used in combination with sulfonylurea drugs, biguanide hypoglycemic agents, α-glycosidase inhibitors and the like.

The compounds of the present invention, per se, may be administered as the medicaments comprising thereof. However, pharmaceutical compositions for oral administrations or parenteral administrations may preferably be administered which can be prepared by methods well known to those skilled in the art. The compounds may also be added to medicaments comprising a thiazoline compound, a substance having insulin-like action or the like used as an agent for treatment of diabetes, and used as pharmaceutical compositions in the forms of so-called combination formulations. Examples of the pharmaceutical compositions suitable for oral administrations include, for example, tablets, capsules, powders, subtilized granules, granules, liquids, syrups and the like. Examples of the pharmaceutical compositions suitable for parenteral administrations include, for example, injections, drip infusions, suppositories, inhalants, eye drops, nasal drops, ointments, creams, transdermal preparations, transmucosal preparations, patches and the like.

The aforementioned pharmaceutical compositions may be prepared by the addition of pharmacologically and pharmaceutically acceptable additives. Examples of the pharmacologically and pharmaceutically acceptable additives include, for example, excipients, disintegrators and disintegrating aids, binders, lubricants, coating agents, colorants, diluents, base materials, dissolving agents and dissolving aids, isotonic agents, pH modifiers, stabilizers, propellants, adhesives and the like.

The doses of the medicament of the present invention are not particularly limited, and suitable doses can readily be suitably chosen for any types of administrations, for example, where the medicament of the present invention alone is administered, where the medicament of the present invention and a medicament comprising a thiazoline compound or a substance having insulin-like action used as an agent for treatment of diabetes are administered as a single combination drug, where the medicament of the present invention and a medicament containing a thiazoline compound or a substance having insulin-like action are used in combination but administered separately. For example, for oral administrations, the medicament may be administered in a dose of 0.01–1,000 mg per day for an adult. However, it is desirable that the doses are suitably increased or decreased depending on, for example, the age, body weight, symptoms of a patient, presence or absence of complications and conditions thereof, purpose of the administration, i.e., therapeutic or preventive purpose. Where the medicament of the present invention is used in combination with a medicament containing a thiazoline compound or a substance having insulin-like action, the medicament of the present invention can be administered in any periods of time, i.e., during the period of administration of a medicament containing a thiazoline compound or a substance having insulin-like action and/or before or after the period.

EXAMPLES

The present invention will be explained more specifically explained with reference to the following examples. However, the scope of the present invention is not limited to these examples. The compound numbers in the examples correspond to those of the aforementioned preferred compounds.

Example 1

Enhancing Effect of Medicaments of the Present Invention on the Differentiation of Precursor Adipocytes into Adipocytes Adipocytes are important for lipid metabolism or energy homeostasis. Their major role is to reserve energy intracellularly as lipids when energy becomes excess, and to mobilize the energy when nutrition is depleted. It has been known that, in the noninsulin dependent diabetes mellitus, hyperglycemia, hyperinsulinism, hyperlipidemia and so forth are remitted by improving the metabolic function of adipocytes. For example, thiazoline compounds which have an action of differentiating precursor adipocytes into adipocytes, e.g. troglitazone, are useful as agents for treatment of diabetes.

Therefore, effect of the medicaments of the present invention on enhancement of differentiation of precursor adipocytes into adipocytes was examined by using an adipocyte strain 3T3L-1 (obtained from Japanese Cancer Research Resource Bank) according to the published method (Endocrinology, 137, 4706, 1996). The cells were cultured in a culture dish having a diameter of 6 cm as a monolayer, and added with HX600, HX-620, HX-630, or HX-640 when the cells reached a density at which the cells began to contact with one another. After the culture for 13 days, lipid droplets in the cells were stained with Oil Red O. The dye was extracted with 1.0 ml of isopropanol (a modified method described in Methods in Enzymology, 32, 192), and absorbance (490 nm) of the extract was measured and used as index of differentiation into adipocytes. As shown in Table 2, HX-600, HX-620, HX-630 and HX-640 strongly promoted the differentiation of precursor adipocyte 3T3L-1 into adipocytes.

TABLE 2

| Test compound | Concentration (M) | Absorbance (490 nm) |
|---|---|---|
| Control |  | 0.266 |
| HX-600 | $10^{-8}$ | 0.274 |
| HX-600 | $10^{-7}$ | 0.445 |
| HX-600 | $10^{-6}$ | 0.690 |
| HX-620 | $10^{-8}$ | 0.225 |
| HX-620 | $10^{-7}$ | 0.308 |
| HX-620 | $10^{-6}$ | 0.543 |
| HX-630 | $10^{-8}$ | 0.298 |
| HX-630 | $10^{-7}$ | 0.471 |
| HX-630 | $10^{-6}$ | 0.745 |
| HX-640 | $10^{-8}$ | 0.365 |
| HX-640 | $10^{-7}$ | 0.694 |
| HX-640 | $10^{-6}$ | 0.825 |

Example 2

Enhancing Effect of the Medicament of the Present Invention on the Inducing Action of Differentiation of Precursor Adipocytes into Adipocytes by a Thiazoline Compound Cells of the adipocyte strain 3T3L1 were cultured in a culture dish having a diameter of 3.5 cm as a monolayer, and added with troglitazone (CS-045), one of the thiazoline compounds used as an agent for treatment of diabetes, and simultaneously with HX-600 when the cells reached a density at which the cells began to contact with one another. The culture was continued for 10 days. As shown in Table 3, HX600 ($10^{-7}$ M) synergistically promoted the action of inducing differentiation into adipocytes by CS-045 ($10^{-7}$ M). The results indicate that the medicament of present invention promoted the enhancing action of the thiazoline compound, and that the medicament is useful for making the thiazoline compound take more efficient therapeutic effect on diabetes.

TABLE 3

| Test compound | Absorbance (490 nm) |
|---|---|
| Control | 0.086 |
| HX-600 ($10^{-7}$M) | 0.131 |
| CS-045 ($10^{-7}$M) | 0.171 |
| HX-600 ($10^{-7}$M) + CS-045 ($10^{-7}$M) | 0.376 |

Example 3

Enhancing Effect of the Medicament of the Present Invention on the Inducement of Differentiation of Precursor Adipocytes into Adipocytes by Insulin Synergistic effect of insulin used for therapeutic treatment of diabetes and the medicament of the present invention was examined. Cells of the adipocyte strain 3T3L-1 were cultured in a culture dish having a diameter of 3.5 cm as a monolayer, and added with 10 µg/ml of insulin and HX-600 ($10^{-6}$ M or $10^{-8}$ M) when the cells reached a density at which the cells began to contact with one another. The culture was continued for 9 days. As shown in Table 4, differentiation into adipocytes induced by the action of insulin was synergistically promoted when HX-600 ($10^{-6}$ M and $10^{-8}$ M) was added. The results indicate that the medicament of present invention enhances the action of insulin, and that the medicament is useful for making insulin take more efficient therapeutic effect on diabetes.

TABLE 4

| Test compound | Absorbance (490 nm) |
|---|---|
| Not added | 0.072 |
| HX-600 ($10^{-8}$M) | 0.118 |
| HX-600 ($10^{-6}$M) | 0.287 |
| Insulin (10 µg/ml) | 0.301 |
| Insulin (10 µg/ml) + HX-600 ($10^{-8}$M) | 0.518 |
| Insulin (10 µg/ml) + HX-600 ($10^{-6}$M) | 0.671 |

Example 4

Hypoglycemic Action of the Medicament of the Present Invention in Diabetes Model Mice Experiments were performed by using diabetic mice hereditarily have pathological conditions of fatness, hyperglycemia, and hyperlipidemia (C57BL/6J-Lepob, female, Jackson Laboratory, 10-week old) according to the method described in the literature (Diabetologia, 14, 141, 1978). Blood samples were collected one day before the start of the administration, and the mice were divided into three groups (one group consisted of 4 or 5 mice). One group was used as a medication group, and each mouse of the group was orally administered with HX-600 suspended in 0.1% carboxymethylcellulose as microparticules (30 mg/kg/day or 100 mg/kg/day) every day for 6 days. Mice of the control group were orally administered with only 0.1% carboxymethylcellulose. On the 6th day after the start of the administration, blood samples were collected from ophthalmic fundus veins.

Blood glucose level was measured by the glucose oxidase method (Fuji Drychem Slide GLU-P), and acylglycerol level was measured by the glycerol phosphate dehydrogenase method (Fuji Drychem Slide TG-P). As a measurement apparatus, Fuji Drychem 5000 was used. As shown in Table 5, the group of mice administered with HX600 (30 mg/kg/day and 100 mg/kg/day) had remarkably lower blood glucose level and acylglycerol level than the control group on the 6th day of the administration. Percentages based on the control group are also indicated. These results demonstrate that the medicament of the present invention has excellent hypoglycemic action, and is useful for preventive and/or therapeutic treatment of diabetes and complications resulting from diabetes, in particular, hyperlipidemia.

TABLE 5

| Test group | Blood glucose level (mg/dl) | Blood acylglyerol level (mg/dl) |
|---|---|---|
| Control | 428 ± 82 | 132 ± 14 |
| 30 mg/kg/day | 258 ± 56 (60.3%) | 105 ± 14 (79.5%) |
| 100 mg/kg/day | 238 ± 59 (55.6%) | 96 ± 11 (72.7%) |

Industrial Applicability

The medicaments of the present invention are useful for therapeutic and/or preventive treatment of diabetes and complications of diabetes, and the medicaments can achieve extremely high preventive and/or therapeutic effect when the medicaments are used in combination with thiazoline compounds, insulin and the like which are conventionally used as agents for treatment of diabetes.

What is claimed is:

1. A method for the therapeutic treatment of diabetes comprising:

administering to a mammal an amount of a medicament effective to treat the diabetes, the medicament comprising as an active ingredient a compound having formula (I):

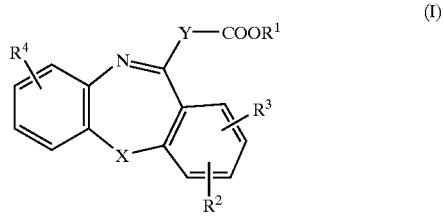

or a compound having formula (II):

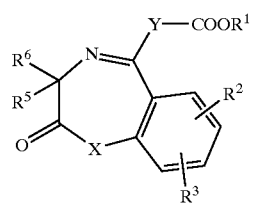

wherein $R^1$ represents hydrogen atom or $C_{1-6}$ alkyl group;
$R^2$ and $R^3$ independently represent hydrogen atom or $C_{1-6}$ alkyl group, or $R^2$ and $R^3$ may combine together with the carbon atoms of the phenyl ring to which $R^2$ and $R^3$ bind to represent a 5- or 6-membered ring which may optionally be substituted with one or more $C_{1-4}$ alkyl groups;
$R^4$ represents hydrogen atom, $C_{1-6}$ alkyl group, $C_{1-6}$ alkoxyl group, hydroxyl group, nitro group, or halogen atom;
$R^5$ represents hydrogen atom, $C_{1-6}$ alkyl group, or aryl-substituted $C_{1-6}$ alkyl group;
$R^6$ represents hydrogen atom or $C_{1-6}$ alkyl group;
X represents —$NR^7$—, —NO—, —O—, —$CHR^7$—, —S—, —SO— or —$SO_2$— in which $R^7$ represents hydrogen atom, $C_{1-6}$ alkyl group, or aryl-substituted $C_{1-6}$ alkyl group; and
Y represents a phenylene group or a pyridinediyl group, a physiologically acceptable salt thereof, and a hydrate thereof and a solvate thereof.

2. The method for the therapeutic treatment of diabetes according to claim 1, wherein the compound of formula (I) is:
4-[5H-2,3-(2,5-dimethyl-2,5-hexano)-5-methyldibenzo[b,e][1,4]diazepin-11-yl]benzoic acid;
4-[5H-2,3-diisopropyl-5-methyldibenzo[b,e][1,4]diazepin-11-yl]benzoic acid;
4-[5H-2-tert-butyl-5-methyldibenzo[b,e][1,4]diazepin-11-yl]benzoic acid;
4-[5H-3,4-(1,4-butano)-5-methyldibenzo[b,e][1,4]diazepin-11-yl]benzoic acid;
4-[5H-2,3-(2,5-dimethyl-2,5-hexano)-5-methyl-8-nitrodibenzo[b,e][1,4]-diazepin-11-yl]benzoic acid;
4-[2,3-(2,5-dimethyl-2,5-hexano)dibenzo[b,f][1,4]oxazepin-11-yl]benzoic acid;
4-[2,3-(2,5-dimethyl-2,5-hexano)dibenzo[b,f][1,4]thiazepin-11-yl]benzoic acid;
5-[5H-2,3-(2,5-dimethyl-2,5-hexano)-5-methyldibenzo[b,e][1,4]diazepin-11-yl]-2-pyridinecarboxylic acid;
6-[5H-2,3-(2,5-dimethyl-2,5-hexano)-5-methyldibenzo[b,e][1,4]diazepin-11-yl]-3-pyridinecarboxylic acid; or
4-[2,3-(2,5-dimethyl-2,5-hexano)dibenzo[b,e]azepin-11-yl]benzoic acid,
a physiologically acceptable salt thereof, and a hydrate thereof and a solvate thereof.

3. The method for the therapeutic treatment of diabetes according to claim 1, wherein the compound of formula (II) is a compound where
X represents —$NR^7$—;
Y represents para-phenylene;
$R^1$ represents hydrogen or methyl;
$R^2$ represents hydrogen, 7-methyl, 8-methyl, 7-ethyl, 7-propyl, or 7-t-butyl;

$R^3$ represents hydrogen, 8-methyl, 9-methyl, 8-ethyl, 8-propyl, or 8-t-butyl;
$R^2$ and $R^3$ may combine together with the carbon atoms at the 7 and 8 position of the phenyl ring to which $R^2$ and $R^3$ bind to represent —$(CH_2)_4$—, or —$C(CH_3)_2CH_2CH_2C(CH_3)_2$—,
$R^5$ represents hydrogen, methyl, ethyl, propyl, t-butyl, or benzyl;
$R^6$ represents hydrogen or methyl; and
$R^7$ represents hydrogen, methyl, isopropyl or benzyl.

4. The method for the therapeutic treatment of diabetes according to claim 3, wherein the compound of formula (II) is:
4-[1,3-dihydro-7,8-(2,5-dimethyl-2,5-hexano)-2-oxo-2H-1,4-benzodiazepin-5-yl]benzoic acid;
4-[1,3-dihydro-7,8-(2,5-dimethyl-2,5-hexano)-1-methyl-2-oxo-2H-1,4-benzodiazepin-5-yl]benzoic acid;
4-[3(S)-methyl-1,3-dihydro-7,8-(2,5-dimethyl-2,5-hexano)-2-oxo-2H-1,4-benzodiazepin-5-yl]benzoic acid;
4-[1,3-dihydro-7,8-(2,5-dimethyl-2,5-hexano)-1-isopropyl-2-oxo-2H-1,4-benzodiazepin-5-yl]benzoic acid;
4-[1-benzyl-1,3-dihydro-7,8-(2,5-dimethyl-2,5-hexano)-2-oxo-2H-1,4-benzodiazepin-5-yl]benzoic acid; or
4-[3(S)-benzyl-1,3-dihydro-7,8-(2,5-dimethyl-2,5-hexano)-2-oxo-2H-1,4-benzodiazepin-5-yl]benzoic acid,
a physiologically acceptable salt thereof, and a hydrate thereof and a solvate thereof.

5. The method for the therapeutic treatment of diabetes according to claim 1, wherein the diabetes is caused by an abnormality of insulin action, by an abnormality of insulin secretion or by nutritional disturbance.

6. The method for the therapeutic treatment of diabetes according to claim 5, wherein the abnormality of insulin action includes a disorder of intracellular glucose utilization, a functional disorder of an insulin receptor, or a structural abnormality of insulin.

7. The method for the therapeutic treatment of diabetes according to claim 5, wherein the abnormality of insulin secretion includes an abnormality of signal transmission.

8. The method for the therapeutic treatment of diabetes according to claim 1, wherein the medicament further comprises a thiazoline compound or a substance having insulin-like action.

9. The method for the therapeutic treatment of diabetes according to claim 8, wherein the thiazoline compound is troglitazone or pioglitazone and the substance having insulin-like action is insulin or glimepiride.

10. The method for the therapeutic treatment of diabetes according to claim 1, wherein the medicament is administered to a mammal in need of said treatment in an amount effective to treat the diabetes.

11. A method for the therapeutic treatment of a complication of diabetes comprising:
administering to a mammal an amount of a medicament effective to treat the complication of diabetes, the medicament comprising as an active ingredient a compound having formula (I):

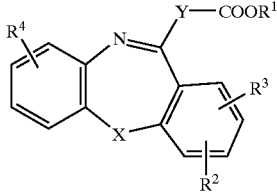 (I)

or a compound having formula (II):

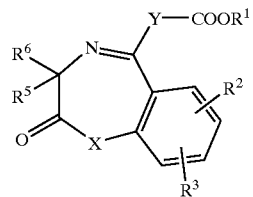 (II)

wherein $R^1$ represents hydrogen atom or $C_{1-6}$ alkyl group; $R^2$ and $R^3$ independently represent hydrogen atom or $C_{1-6}$ alkyl group, or $R^2$ and $R^3$ may combine together with the carbon atoms of the phenyl ring to which $R^2$ and $R^3$ bind to represent a 5- or 6-membered ring which may optionally be substituted with one or more $C_{1-4}$ alkyl groups;

$R^4$ represents hydrogen atom, $C_{1-6}$ alkyl group, $C_{1-4}$ alkoxyl group, hydroxyl group, nitro group, or halogen atom;

$R^5$ represents hydrogen atom, $C_{1-6}$ alkyl group, or aryl-substituted $C_{1-6}$ alkyl group;

$R^6$ represents hydrogen atom or $C_{1-6}$ alkyl group;

X represents —$NR^7$—, —NO—, —O—, —$CHR^7$—, —S—, —SO— or —$SO_2$— in which $R^7$ represents hydrogen atom, $C_{1-6}$ alkyl group, or aryl-substituted $C_{1-6}$ alkyl group; and Y represents a phenylene group or a pyridinediyl group, a physiologically acceptable salt thereof, and a hydrate thereof and a solvate thereof.

12. The method for the therapeutic treatment of a complication of diabetes according to claim 11, wherein the compound of formula (I) is:

4-[5H-2,3-(2,5-dimethyl-2,5-hexano)-5-methyldibenzo[b,e][1,4]diazepin-11-yl]benzoic acid;

4-[5H-2,3-diisopropyl-5-methyldibenzo[b,e][1,4]diazepin-11yl]benzoic acid;

4-[5H-2-tert-butyl-5-methyldibenzo[b,e][1,4]diazepin-11-yl]benzoic acid;

4-[5H-3,4-(1,4-butano)-5-methyldibenzo[b,e][1,4]diazepin-11-yl]benzoic acid;

4-[5H-2,3-(2,5-dimethyl-2,5-hexano)-5-methyl-8-nitrodibenzo[b,e][1,4]-diazepin-11-yl]benzoic acid;

4-[2,3-(2,5-dimethyl-2,5-hexano)dibenzo[b,f][1,4]oxazepin-11-yl]benzoic acid;

4-[2,3-(2,5-dimethyl-2,5-hexano)dibenzo[b,f][1,4]thiazepin-11-yl]benzoic acid;

5-[5H-2,3-(2,5-dimethyl-2,5-hexano)-5-methyldibenzo[b,e][1,4]diazepin-11-yl]-2-pyridinecarboxylic acid;

6-[5H-2,3-(2,5-dimethyl-2,5-hexano)-5-methyldibenzo[b,e][1,4]diazepin-11-yl]-3-pyridinecarboxylic acid; or 4-[2,3-(2,5-dimethyl-2,5-hexano)dibenzo[b,e]azepin-11-yl]benzoic acid, a physiologically acceptable salt thereof, and a hydrate thereof and a solvate thereof.

13. The method for the therapeutic treatment of a complication of diabetes according to claim 11, wherein the compound of formula (II) is a compound where X represents —$NR^7$—;

Y represents para-phenylene;

$R^1$ represents hydrogen or methyl;

$R^2$ represents hydrogen, 7-methyl, 8-methyl, 7-ethyl, 7-propyl, or 7-t-butyl;

$R^3$ represents hydrogen, 8-methyl, 9-methyl, 8-ethyl, 8-propyl, or 8-t-butyl;

$R^2$ and $R^3$ may combine together with the carbon atoms at the 7 and 8 position of the phenyl ring to which $R^2$ and $R^3$ bind to represent —$(CH_2)_4$—, or —$C(CH_3)_2CH_2CH_2C(CH_3)_2$—;

$R^5$ represents hydrogen, methyl, ethyl, propyl, t-butyl, or benzyl;

$R^6$ represents hydrogen or methyl; and $R^7$ represents hydrogen, methyl, isopropyl or benzyl.

14. The method for the therapeutic treatment of a complication of diabetes according to claim 13, wherein the compound of formula (II) is:

4-[1,3-dihydro-7,8-(2,5-dimethyl-2,5-hexano)-2-oxo-2H-1,4-benzodiazepin-5-yl]benzoic acid;

4-[1,3-dihydro-7,8-(2,5-dimethyl-2,5-hexano)-1-methyl-2-oxo-2H-1,4-benzodiazepin-5-yl]benzoic acid;

4-[3(S)-methyl-1,3-dihydro-7,8-(2,5-dimethyl-2,5-hexano)-2-oxo-2H-1,4-benzodiazepin-5-yl]benzoic acid;

4-[1,3-dihydro-7,8-(2,5-dimethyl-2,5-hexano)-1-isopropyl-2-oxo-2H-1,4-benzodiazepin-5-yl]benzoic acid;

4-[1-benzyl-1,3-dihydro-7,8-(2,5-dimethyl-2,5-hexano)-2-oxo-2H-1,4-benzodiazepin-5-yl]benzoic acid; or 4-[3(S)-benzyl-1,3-dihydro-7,8-(2,5-dimethyl-2,5-hexano)-2-oxo-2H-1,4-benzodiazepin-5-yl]benzoic acid, a physiologically acceptable salt thereof, and a hydrate thereof and a solvate thereof.

15. The method for the therapeutic treatment of a complication of diabetes according to claim 11, wherein the complication is hyperlipidemia.

16. The method for the therapeutic treatment of a complication of diabetes according to claim 11, wherein the medicament further comprises a thiazoline compound or a substance having insulin-like action.

17. The method for the therapeutic treatment of a complication of diabetes according to claim 16, wherein the thiazoline compound is troglitazone or pioglitazone and the substance having insulin-like action is insulin or glimepiride.

18. The method for the therapeutic treatment of a complication of diabetes according to claim 11, wherein the medicament is administered to a mammal in need of said treatment in an amount effective to treat the complication of diabetes.

19. A method for the therapeutic treatment of hyperlipidemia comprising:

administering to a mammal an amount of a medicament effective to treat the hyperlipidemia, the medicament comprising as an active ingredient a compound which is:

4-[5H-2,3-(2,5-dimethyl-2,5-hexano)-5-methyldibenzo[b,e][1,4]diazepin-11-yl]benzoic acid;

4-[5H-2,3-diisopropyl-5-methyldibenzo[b,e][1,4]diazepin-11-yl]benzoic acid;

4-[5H-2-tert-butyl-5-methyldibenzo[b,e][1,4]diazepin-11-yl]benzoic acid;

4-[5H-3,4-(1,4-butano)-5-methyldibenzo[b,e][1,4]diazepin-11-yl]benzoic acid;

4-[5H-2,3-(2,5-dimethyl-2,5-hexano)-5-methyl-8-nitrodibenzo[b,e][1,4]-diazepin-11-yl]benzoic acid;

4-[2,3-(2,5-dimethyl-2,5-hexano)dibenzo[b,f][1,4]oxazepin-11-yl]benzoic acid;

4-[2,3-(2,5-dimethyl-2,5-hexano)dibenzo[b,f][1,4]thiazepin-11-yl]benzoic acid;

5-[5H-2,3-(2,5-dimethyl-2,5-hexano)-5-methyldibenzo[b,e][1,4]diazepin-11-yl]-2-pyridinecarboxylic acid;

6-[5H-2,3-(2,5-dimethyl-2,5-hexano)-5-methyldibenzo[b,e][1,4]diazepin-11-yl]-3-pyridinecarboxylic acid;

4-[2,3-(2,5-dimethyl-2,5-hexano)dibenzo[b,e]azepin-11-yl]benzoic acid;

4-[1,3-dihydro-7,8-(2,5-dimethyl-2,5-hexano)-2-oxo-2H-1,4-benzodiazepin-5-yl]benzoic acid;

4-[1,3-dihydro-7,8-(2,5-dimethyl-2,5-hexano)-1-methyl-2-oxo-2H-1,4-benzodiazepin-5-yl]benzoic acid;

4-[3(S)-methyl-1,3-dihydro-7,8-(2,5-dimethyl-2,5-hexano)-2-oxo-2H-1,4-benzodiazepin-5-yl]benzoic acid;

4-[1,3-dihydro-7,8-(2,5-dimethyl-2,5-hexano)-1-isopropyl-2-oxo-2H-1,4-benzodiazepin-5-yl]benzoic acid;

4-[1-benzyl-1,3-dihydro-7,8-(2,5-dimethyl-2,5-hexano)-2-oxo-2H-1,4-benzodiazepin-5-yl]benzoic acid; or 4-[3(S)-benzyl-1,3-dihydro-7,8-(2,5-dimethyl-2,5-hexano)-2-oxo-2H-1,4-benzodiazepin-5-yl]benzoic acid, a physiologically acceptable salt thereof, and a hydrate thereof and a solvate thereof, the medicament further comprising a thiazoline compound or a substance having insulin-like action.

20. The method for the therapeutic treatment of hyperlipidemia according to claim 19, wherein the medicament is administered to a mammal in need of said treatment in an amount effective to treat the hyperlipidemia.

* * * * *

UNITED STATES PATENT AND TRADEMARK OFFICE
CERTIFICATE OF CORRECTION

PATENT NO.    : 6,458,782 B1         Page 1 of 1
DATED         : October 1, 2002
INVENTOR(S)   : H. Kagechika et al.

It is certified that error appears in the above-identified patent and that said Letters Patent is hereby corrected as shown below:

Column 15,
Line 31, "$C_{1-4}$ alkoxyl group" should be -- $C_{1-6}$ alkoxyl group --.

Signed and Sealed this

Twenty-fourth Day of June, 2003

JAMES E. ROGAN
*Director of the United States Patent and Trademark Office*